United States Patent [19]
Bergeron

[11] 3,932,476
[45] Jan. 13, 1976

[54] PREPARATION OF FATTY ACID AMIDES
[75] Inventor: Charles R. Bergeron, Baton Rouge, La.
[73] Assignee: Ethyl Corporation, Richmond, Va.
[22] Filed: July 2, 1973
[21] Appl. No.: 375,961

[52] U.S. Cl............................ 260/404; 260/561 R
[51] Int. Cl.²...................................... C07C 103/00
[58] Field of Search....................... 260/404, 561 R

[56] References Cited
UNITED STATES PATENTS

| | | | |
|---|---|---|---|
| 3,072,725 | 1/1963 | Surman........................... | 260/561 R |
| 3,324,179 | 6/1967 | Scholz............................. | 260/404 X |
| 3,342,862 | 9/1967 | Board et al. .................... | 260/561 R |
| 3,538,159 | 11/1970 | Duffy.............................. | 260/404 X |

*Primary Examiner*—Ethel G. Love
*Attorney, Agent, or Firm*—Donald L. Johnson; John F. Sieberth; Shelton B. McAnelly

[57] ABSTRACT

It is disclosed that amides are readily prepared by reacting an ester of a volatile alcohol with a volatile amine reactant in an anhydrous system and at moderate pressure. Excess amine reactant is fed to the reaction system and allowed to escape therefrom in the course of the reaction to remove alcohol liberated during the reaction.

10 Claims, No Drawings

PREPARATION OF FATTY ACID AMIDES

BACKGROUND OF THE INVENTION

1. Field of the Invention

This invention relates to the preparation of amides of fatty acids having from about 8 to about 20 carbon atoms. In particular, the invention relates to a process for producing the foregoing amides from esters by reaction thereof with amine reactant in an anhydrous system.

2. Description of the Prior Art

The preparation of fatty acid amides from fatty acid esters can be accomplished by several processes known in the prior art. In the process of U.S. Pat. No. 3,253,006, the reaction is performed in the presence of what is described as a highly critical amount of water and under high pressures of above 1000 psig. Unfortunately the high pressures used necessitate expensive equipment capable of withstanding high pressure operation and the presence of water produces a very corrosive system requiring special materials of construction.

In other prior art the use of solvents other than water is disclosed. For example, U.S. Pat. No. 2,464,094 discloses the use of alcohol solvents such as methanol fed to the reaction system. Although the patent does discuss the subsequent removal of methanol, it does not suggest removal to the extent or in the manner disclosed herein. The problem of slow reaction rate in amidation of esters is evident in the prior art search for catalysts as disclosed, for example, in the main force of U.S. Pat. No. 2,464,094. Another patent dealing with solvents deliberately or fortuitously present is U.S. Pat. No. 2,504,427. Although this patent speaks of distilling off the by-product water or alcohol or using complexing agents, such is not undertaken until after the reaction is terminated.

In some instances, the use of catalysts such as salts or alkali metals is regarded as very much undesired. Not only is this an item of expense but also there is the problem of removal of the catalyst after its presence is no longer desired. A process that can be enhanced with catalyst yet which can be performed satisfactorily without catalyst can be useful in various ways.

Other prior art includes processes in which operation is at low pressures and in the absence of water; however, as discussed in the aforementioned U.S. Pat. No. 3,253,006, the prior art operations under anhydrous conditions have been characteristically slow requiring reaction times of as much as several days. Such long reaction times are undesired for obvious reasons because of the adverse effect thereof upon the ability to produce amides at low cost.

It is accordingly an object of the present invention to provide a process for producing amides which does not require either high pressure of operation or catalysts.

Another object of the present invention is to provide a process for producing amides using anhydrous conditions. Another object of the present invention is to provide a process for producing amides that does not require solvents.

Another object of the present invention is to provide a process for producing amides by reaction of ester and amine reactant wherein high reaction rate is obtained in an anhydrous system at low pressure and in which amine reactant is used as a stripping agent to remove reaction by-products.

Another object of the present invention is to provide a process for producing amides from esters of fatty acids and an amine reactant wherein alcohol liberated from the esters in the course of the reaction is removed from the system by stripping with excess amine reactant.

Summary

The present invention provides a process for producing amides of fatty acids in which is achieved a high reaction rate in an anhydrous system without requiring the presence of water or catalyst or the use of pressures in excess of about 500 lbs psi and which does not involve severely corrosive materials.

Preferably, in the process of the present invention amides are produced by reacting fatty acid esters with an amine reactant which is more volatile than the feed esters or the amide product. Preferably, the esters used have alcohol components which have a substantial vapor pressure under the conditions of operation. This volatility situation produces a two phase system through which is passed a stream of the amine reactant to strip out the by-product alcohol liberated from the esters as a result of the reaction. In this way the by-product alcohol is rapidly removed from the system achieving a high reaction rate at comparatively low pressure. Surprisingly, it has been discovered that despite the two phase system, a high reaction rate is achieved which is enhanceable by catalysts but does not require catalyst. The reaction is performed in any suitable apparatus typically in batchwise operation as in a stirred pot or in a continuous process as in an autoclave or in a tower type reactor. The recovered amine reactant passed through the system to remove the liberated alcohol can be utilized in any suitable manner but preferably it is treated to remove the alcohol and is then recycled to the reaction system for reaction and removal of additional by-product alcohol.

The present invention provides a process for preparing an amide of a fatty acid having from about 8 to about 20 carbon atoms per molecule comprising reacting in a substantially anhydrous system (1) an ester of a fatty acid having from about 8 to about 20 carbon atoms per molecule and of a lower alcohol having from 1 to about 6 carbon atoms per molecule with (2) ammonia or a mono or dialkyl methyl or ethyl amine fed at a rate in excess of the rate of reaction thereof, the excess of (2) being removed from the system during the reaction to remove from the system the lower alcohol component released from the ester in the reaction.

In a preferred aspect of the present process the excess ammonia or amine removed from the system is treated to remove the alcohol and the ammonia or amine is recycled to the reaction system.

In a preferred aspect of the present process the ester is an ester of methanol, ethanol, propanol or butanol.

In a preferred aspect of the present process the ester is an ester of methanol.

In a preferred aspect of the present process ammonia is reacted with the ester.

In a preferred aspect of the present process the ester reacted is an ester of pure or of mixed fatty acids having predominantly from about 10 to about 18 carbon atoms per molecule.

In a preferred aspect of the present process the ester reacted is of the formula

wherein
R is hydrogen or alkyl having from 1 to about 8 carbon atoms,
R' is alkyl, alkenyl or polyalkenyl having from about 6 to about 18 carbon atoms,
R'' is ($C_nH_{2n+1}$) where $n$ is 1, 2, 3 or 4.

In a preferred aspect of the present process the ester reacted is an ester of undecanoic acid, 2-methyl decanoic acid, 2-ethyl nonanoic acid, tridecanoic acid, 2-methyl dodecanoic acid, 2-ethyl undecanoic acid, pentadecanoic acid, 2-methyl tetradecanoic acid, or 2-ethyl tridecanoic acid.

Ester reactants for the present process are preferably lower alkyl, e.g., methyl, esters of fatty acids having from about 8 to about 20 carbon atoms per molecule. In reaction with amine in accordance with the present process, such esters produce amides having a long chain organic radical corresponding to the organic radical of the acid component of the starting ester.

It is readily seen that one can selectively produce a desired amide product by using a starting ester whose organic acid radical or acyl group is the same as that desired for the product amide.

The fatty acid radical or acyl group of the ester reactant can be any group which does not react adversely or decompose under the conditions involved. The radical can be saturated or unsaturated, including polyunsaturated of natural source or synthetic source, having odd or even numbers of carbon atoms and straight chain, branched chain, cyclic or aromatic carbon skeletal structure. Where the carbon skeletal chain is branched, the structures may have one or plural branches with similar or different lengths of side chains. Preferred branching when present is that of a single methyl group in the position alpha to the carbon atom of the carboxyl group; however, acid radicals with more remote or plural branching and with longer side chains than methyl such as 2-ethyl hexanoic, 1-ethyl decanoic, 1-methyl-4-ethyl octanoic, and the like are typical.

Examples of fatty acids whose acid radicals are suitable for esters used in the present process include caprylic acid, capric acid, lauric acid, myristic acid, palmitic acid, stearic acid, oleic acid, linoleic acid, and linolenic acid. Other examples are those of mixtures of the fatty acids derived from natural fats and oils such as coconut oil, tallow, palm kernel oil, soybean oil, whale oil, fish oil, tall oil, and other natural oils that are derived from animal, vegetable or marine sources. Synthetic fatty acid radicals can be obtained via the oxidation of alcohols, ketones, aldehydes or hydrocarbons, as well as by other processes such as the oxo process reaction of olefins with carbon monoxide. When the olefin-carbon monoxide reaction is performed catalytically in the presence of lower alcohol, excellent starting esters for the present amidation reaction are obtained directly, a lower alcohol being selected for that process which is suitable for the herein-stated requirements of the present process. The two processes can be operated in conjunction with each other whereby alcohol recovered from the stripping amine reactant is recycled to the process that produces the esters fed to the amidation. For such a combination, methanol is a preferred alcohol.

Suitable esters for the process of the present invention may be reacted with the amine reactant as mixtures or as pure esters depending upon the source and structure of the esters and the relationship thereof to the product desired. Amide products therefore can be produced which are pure in a sense of having substantially 100 percent content of a single acyl radical or they can be mixtures with two or more acyl radicals present. Of course, amide mixtures can be obtained by blending amides or mixtures of amides produced in separate amidation operations.

Preferred ester reactants used are those whose alcohol constituency R''OH after release from the ester is volatile enough to be readily stripped from the reaction system by the passage therethrough of a gaseous or vapor stream of amine reactant. Although other stripper gases can be used, the use of amine reactant is particularly desirable because of avoidance of contamination and purification problems. In general, the stripping form of operation places the requirement for the alcohol component of esters used that they be lower alcohols having from one to about 6 carbon atoms per molecule, preferably methanol, ethanol, n-propanol and n-butanol. Preferred alcohols are primary alcohols because of the ease of esterification of such alcohols with fatty acids to produce the esters. Thus, although suitable alcohols include isopropanol, isobutanol, t-butanol and the like, in general primary alcohols are preferred as are corresponding esters. It is readily evident that esters whose alcohol component is a higher order alcohol such as a diol or a triol or the like, such as ethylene glycol or glycerol, are also suitably used in appropriate instances; however, from volatility considerations to facilitate the formation of the desired vapor phase for stripping at low temperatures, thereby permitting operation at low pressure, it is preferred that the alcohol component of esters reacted be alkanols.

For the most part, the ester is a reactive carrier for the organic acid group. The main requirements for the alcohol constituency of the ester are that it be an alcohol which is readily esterified with the desired acid and which is also readily stripped out as by the flow of gaseous or vaporized amine reactant or stripper gas through the reaction system. A particularly preferred alcohol component of ester reactants is methanol because of the low molecular weight thereof, the ease of esterification with acids and ease of reaction in a system with olefins and CO using cobalt carbonyl and similar catalysts to produce esters and convenient volatility particularly in systems where the amine reactant is ammonia or a methyl amine containing a reactive hydrogenation.

Preferred amine reactants suitable for use in the present invention are ammonia or lower organo amines which are suitably volatile to be removed from the system under convenient conditions of operation particularly in regard to temperature and pressure and which contain at least one reactive hydrogen atom per molecule. Vapor pressure properties of the various amines are known. Preferred amines include ammonia and primary or secondary methyl or ethyl amines such as monomethyl (primary) amine and dimethyl (secondary) amine. In general, the choice as to whether ammonia or primary or secondary amine or a mixture of such amine reactants is used depends largely upon the desired configuration of the portion of the product amide molecules exclusive of the organic acid radical portion thereof. Where it is desired to produce a simple amide product, (acyl-NH$_2$) it is of course evident that ammonia is the desired amine reactant. If it is desired to produce an organo amide product such as a methyl or ethyl amide,

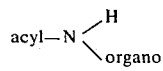

or

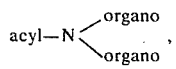

a reactive methyl or ethyl amine or a mixed alkyl secondary amine such as methyl ethyl amine is used. In general, the preferred organo amine reactant is monomethyl (primary) amine.

It is evident that the foregoing exemplary ammonia and amine reactants; viz. methyl amine, dimethyl amine, ethyl amine, diethyl amine and methyl ethyl amine are materials with a substantial vapor pressure at temperatures discussed hereinafter making such materials suitable amine reactants for use in the present process. Preferred amine reactants are ammonia or methyl amines because of the ease of reaction, high volatility and the excellence of the products in various customary uses of amides.

In some instances it is desirable to use an auxiliary stripping agent. Such is particularly useful when using organo amine reactants which have a low vapor pressure under the conditions of operation. Typical auxiliary stripping agents are inert and of high vapor pressure such as $CO_2$, $N_2$, $CH_4$ and the like. Operation without auxiliary stripping agents is particularly preferred because of the problem of contamination, separation, recovery and reduced space utilization factors in reactors and associated systems.

The temperature of operation is from about 100° to about 250°C, preferably from about 150° to about 225°C. Below about 90°C the reaction rate is generally too low to be practical while at temperatures above about 250°C, undesired side reactions are experienced.

Pressures are not critical and range from about 100 psig up to about autogenous pressure. Preferably pressures are from about 200 to about 500 psig to avoid the need for high pressure equipment and retain the amine reactant present in suitable proportions, relative to the ester and to the alcohol released. The pressures of this system are substantially lower than the 1000–2000 psig autogenous pressures experienced using a closed system without the stripping action.

Preferred conditions for use with ammonia as amine reactant and methyl esters of C$_8$ to C$_{20}$ acids are temperatures of from about 150° to about 225°C, pressures of from about 200 to about 350 psig.

Reaction time is not critical and depends largely upon temperature and the degree of completion of reaction desired. Typical reaction times range from about 10 minutes up to about 20 hours, with reaction times of from about 1 to about 6 hours preferred.

Where the use of catalysts is desired, known prior art catalysts such as alkali metals such as sodium, organic or inorganic salts, bases and the like may be used. Catalysts may be fed as such or generated in situ, for example, by feeding acetic acid which reacts with amine reactant such as ammonia to produce ammonium acetate catalyst.

The proportions of ester and amine reactant reacted are preferably about stoichiometric, i.e., enough amine reactant is fed to react with all the ester fed. Where the amine is in the vapor phase and the ester is in the liquid phase, it is evident that the reaction system generally has present an excess of ester at all times and that the amount of amine reactant fed over the course of the reaction will be an excess relative to the amount of ester fed. The feed rate for the amine reactant is preferably determined on the basis of a rate that will maintain the concentration of the released alcohol at a low level in the reaction system. As a practical matter, this is determined by the ratio of amine reactants to alcohol in the off-gas. In general, the amount of alcohol in the off-gas is held below 50 percent on a mol basis, preferably below 10 percent, more preferably below 2 percent, and even lower particularly where a recycle system is used to separate the alcohol from the amine reactant and recycle the amine reactant to the reaction system. Thus, it is typical to feed over a several hour reaction period batch process or in a continuous process 5 to 100 mols of amine reactant per mol of ester fed.

The following examples indicate preferred embodiments and aspects of the present invention.

EXAMPLE I

A 300 ml titanium autoclave equipped with an agitator, heater, thermometer, back pressure regulator and an ammonia feed system was used.

To the autoclave was charged 77 grams (385 millimols) of $C_{10}H_{21}COOCH_3$ (mol. wt. 200). The back pressure regulator was set to 240 psig. The autoclave was heated to 150°C and ammonia flow through the system was started at a flow rate of about 78 grams per hour. The autoclave was heated to 225°C and held for 4.5 hours. The product was cooled and analyzed by NMR (nuclear magnetic resonance) and IR (infrared).

The NMR analysis showed 98 mol percent amide and 2 mol percent ester giving a conversion of 98 percent. The IR analysis showed very little ester and no nitrile. In other words, the reaction was virtually complete to the desired product with losses and by-product formation held low.

EXAMPLE II

Example I was repeated using 100 grams (500 millimols) of $C_{10}H_{21}COOMe$ and a temperature of 200°C. The ammonia feed rate was about 16 grams per hour.

Analysis of the product by NMR showed 86 mol percent amide and 14 mol percent ester. I.R. indicated that no nitrile was present.

EXAMPLE III

Example I was repeated using 86.5 grams (379 millimols) of $C_{12}H_{25}COOCH_3$.

The autoclave was heated to 200°C for 3 hours. The ammonia rate was 13–17 grams per hour.

The product analyzed by NMR showed 78 mol percent amide and 22 mol percent ester for a conversion of 78 percent. No acid was detected by NMR or IR analysis. The yield was substantially quantitative.

EXAMPLE IV

Example I was repeated using 8.8 mol percent ammonium acetate as a catalyst produced by feeding acetic acid.

A 300 ml titanium autoclave was charged with 60 grams (300 millimols) of $C_{10}H_{21}COOCH_3$ and 1.75 grams (29 millimols) of acetic acid.

The autoclave was heated to a nominal 225°C; however, in the course of the reaction the temperature dropped to 180°C for about 10 minutes and was raised to about 240°C for 5–10 minutes. Reaction time was 190 minutes. Pressure was 240 psig and the ammonia rate was about 5 mol per hour.

The product NMR did not show any ester present; however, a small nitrile band was detected at 4.45$\mu$, apparently due to the heating at 240°C.

EXAMPLE V

Example IV was repeated using 17.5 millimols of acetic acid to form ammonium acetate as catalyst. Pressure was 90 psig, temperature was 175°C and reaction time was 6 hours. Ammonia flow rate was 0.75 mol per hour.

Analysis of the product by NMR gave 63 wt. percent amide and 37 wt. percent ester. No acid was detected by IR. Conversion was 66 percent, yield 92.0 percent. Material balance showed 95 percent recovery.

EXAMPLE VI

Example V was repeated without catalyst. 97 Grams (425 millimols) of $C_{12}H_{25}COOCH_3$ was fed.

The product analyzed 56.5 mol percent (55 wt. percent) amide and 43.5 mol percent (45 wt. percent) ester.

Conversion was 60 percent, amide yield 89 percent.

EXAMPLE VII

In a comparative run, the titanium autoclave was charged with 22.8 grams (100 millimols) of $C_{12}H_{25}COOCH_3$, 35 milliliters of $NH_4OH$ and 50 milliliters of ethylene glycol. Reaction was at 175°C and 340 psig for 6 hours, and without catalyst. This represents an aqueous system using a solvent.

After the reaction, the autoclave contents was transferred to 300 ml 6N HCl, the resulting solids filtered and washed with water. The filtrate was extracted with ether and the extracts washed twice with water, dried with $Na_2SO_4$ and evaporated. The solids from the ether extraction procedure and the solids from the filtration were combined and dried on a rotary evaporator to give 20 grams of crude product. NMR analysis showed no carboxylic protons and only a little ester. The product was dissolved in benzene and the amide filtered. The recovery was less than 70 percent.

EXAMPLE VIII

In a comparative run, 22.8 g (100 millimols) of $C_{12}H_{25}COOCH_3$, 1000 millimols of $NH_4OH$, 67 milliliters of $CH_3OH$ and 0.5 gram (8 millimols) of $CH_3COOH$ were added to a 300 ml titanium autoclave. The autoclave was pressured to 100 psig with nitrogen and heated to 175°C for 4.16 hrs reaction time.

After cooling, the autoclave was washed out with water and filtered into excess 6N HCl to control foaming of the ammonium carboxylate salt. The white solid material was dried overnight at 95°C in an oven and then weighed giving 7.6 grams.

The filtrate was extracted with ether and the extracts were washed with saturated brine, dried with $CaSO_4$ and evaporated to give 13.6 grams of a semi-solid liquid. NMR analysis indicated the following weight percents present.

| | | |
|---|---|---|
| $RCOOCH_3$ | — | 23 percent |
| $RCOOH$ | — | 63 percent |
| $RCONH_2$ | — | 14 percent |
| Calculations indicated: | | |
| Conversion | — | 86 percent |
| Yield ($RCONH_2$) | — | 52 percent |
| Yield ($RCOOH$) | — | 46 percent |

The amount of catalyst ($NH_4OOCCH_3$) was 7.4 mol percent based on ester fed. The mol ratio of $NH_3:RCOOCH_3$ was 10:1. The solvent was 50 percent aqueous $CH_3OH$ (water present in $NH_4OH$).

EXAMPLE IX

Example VIII was repeated without the catalyst.
NMR analysis indicated the following weight percent present:

| | | |
|---|---|---|
| $RCOOCH_3$ | — | 25 percent |
| $RCOOH$ | — | 63 percent |
| $RCONH_2$ | — | 12 percent |
| Calculations indicated: | | |
| Conversion | — | 86 percent |
| Yield ($RCONH_2$) | — | 47 percent |
| Yield ($RCOOH$) | — | 46 percent |

EXAMPLE X

Example IX was repeated using ethyl alcohol as diluent. Results were similar.

EXAMPLE XI

13 Grams (57 millimols) $C_{12}H_{25}COOCH_3$, 13 grams (764 millimols) of $NH_3$, 140 ml of $CH_3OH$ and 0.2 gram (3.3 millimols) of $CH_3COOH$ were added to the 300 ml titanium autoclave, the autoclave pressured to 100 psig with nitrogen, and the autoclave heated to 175°C for 4.16 hrs reaction time. The autoclave was cooled and the homogeneous solution was evaporated to give a semi-solid product.

Ether was added and the solids were filtered. The filtrate was evaporated, more ether added and filtration was done again. The solids (amide) weighed 2.6 grams.

The ether solution was evaporated to give 9.8 grams of liquid. NMR indicated only methyl ester. Calculations gave:

| | | |
|---|---|---|
| Conversion | — | 24.6 percent |
| Yield ($RCONH_2$) | — | 87 percent |
| Mol Ratio $NH_3:RCOOCH_3 = 13.4:1$ | | |
| Catalyst | — | 5.5 mol percent |

I claim:

1. A process for preparing an amide of a fatty acid having from about 8 to about 20 carbon atoms per molecule comprising reacting in a substantially anhydrous system (1) an ester of a fatty acid having from about 8 to about 20 carbon atoms per molecule and of a lower alcohol having from 1 to about 6 carbon atoms per molecule with (2) ammonia or a mono or dialkyl methyl or ethyl amine fed at a rate in excess of the rate of reaction thereof, the excess of (2) being removed from the system during the reaction to remove from the system the lower alcohol component released from the ester in the reaction.

2. The process of claim 1 wherein the excess ammonia or methyl or ethyl amine removed from the system is treated to remove the alcohol and the ammonia or methyl or ethyl amine is recycled to the reaction sys- 3. The process of claim 1 wherein the ester is an ester of methanol, ethanol, propanol or butanol.

4. The process of claim 1 wherein the ester is an ester of methanol.

5. The process of claim 1 wherein ammonia is reacted with the ester.

6. The process of claim 1 wherein the ester reacted is an ester of mixed fatty acids having predominantly from about 10 to about 18 carbon atoms per molecule.

7. The process of claim 1 wherein the ester reacted is of the formula

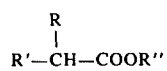

wherein

R is hydrogen, or alkyl having from 1 to about 8 carbon atoms,

R' is alkyl, alkenyl, or polyalkenyl having from about 6 to about 18 carbon atoms, R'' is $C_nH_{2n+1}$ where $n$ is 1, 2, 3 or 4.

8. The process of claim 1 wherein the ester reacted is an ester of oleic acid, linoleic acid or linolenic acid.

9. The process of claim 1 wherein the ester reacted is an ester of undecanoic acid, 2-methyl decanoic acid, 2-ethyl nonanoic acid, tridecanoic acid, 2-methyl dodecanoic acid, 2-ethyl undecanoic acid, pentadecanoic acid, 2-methyl tetradecanoic acid, or 2-ethyl tridecanoic acid.

10. In a process for producing amides by the reaction of fatty acid esters and an amine reactant, the improvement wherein the reaction is conducted in an anhydrous reaction system under conditions wherein ester and amide are substantially in the liquid phase and amine is in the vapor phase and amine is bled from said system during the reaction to strip away from said system alcohol liberated from the esters by the reaction.

* * * * *